United States Patent [19]

Kamachi et al.

[11] Patent Number: 5,143,911
[45] Date of Patent: Sep. 1, 1992

[54] ANTIBIOTIC C-3 DI-HYDROXYPHENYL SUBSTITUTED CEPHALOSPORIN COMPOUNDS, COMPOSITIONS AND METHOD OF USE THEREOF

[75] Inventors: Hajime Kamachi, Chiba; Kiyoto Imae, Kawasaki; Takaaki Okita, Tokyo, all of Japan

[73] Assignee: Bristol-Myers Squibb Company, New York, N.Y.

[21] Appl. No.: 572,516

[22] Filed: Aug. 23, 1990

[51] Int. Cl.$^5$ ............... C07D 501/24; A61K 31/545
[52] U.S. Cl. ............................... 514/202; 540/222
[58] Field of Search ............... 540/221, 222; 514/202

[56] References Cited

U.S. PATENT DOCUMENTS

| | | | |
|---|---|---|---|
| 4,486,586 | 12/1984 | Narita et al. | 544/22 |
| 4,751,295 | 6/1988 | Oka et al. | 540/222 |
| 4,874,856 | 10/1989 | Imura et al. | 540/222 |

FOREIGN PATENT DOCUMENTS

| | | |
|---|---|---|
| 030630 | 11/1981 | European Pat. Off. . |
| 0265185 | 4/1988 | European Pat. Off. . |
| 0329785 | 8/1989 | European Pat. Off. . |
| 408034 | 1/1991 | European Pat. Off. . |
| 1151586 | 6/1989 | Japan . |
| 2069484 | 3/1990 | Japan . |

Primary Examiner—Nicholas S. Rizzo
Attorney, Agent, or Firm—William T. Han

[57] ABSTRACT

The present invention relates to new cephalosporins of the Formula wherein
Y is N or CH;
$R^1$ is hydrogen, a straight, branched, or cyclic lower alkyl group having up to six carbon atoms or a radical of the formula $$-\underset{R^4}{\underset{|}{\overset{R^3}{\overset{|}{C}}}}-CO_2H$$

in which $R^3$ and $R^4$ are each independently hydrogen, methyl, or ethyl, or $R^3$ and $R^4$ taken together with the carbon atom to which they are attached, may be a cycloalkylidene ring containing from 3 to 5 carbon atoms;
$R^2$ is a radical selected from the group consisting of and in which $R^5$ is hydrogen or acetyl.

In another aspect, this invention relates to processes for the preparation of the compounds of Formula I, to pharmaceutical compositions containing at least one compound of Formula I, and to intermediates in their preparation.

21 Claims, No Drawings

ANTIBIOTIC C-3 DI-HYDROXYPHENYL SUBSTITUTED CEPHALOSPORIN COMPOUNDS, COMPOSITIONS AND METHOD OF USE THEREOF

BACKGROUND OF THE INVENTION

The field of this invention is cephalosporins which contain propenyl and di-hydroxyphenyl (catechol) moieties on the three position, their antibiotic use and compositions therefor.

In the antibiotic arts, there has long been a need for new and effective antibiotic compounds. Due to rapid changes in the pathogens, for which treatment with the antibiotic compounds are required, the older and more used antibiotics often become either ineffective or significantly less effective against the pathogens. Effective antibiotics are therefore in constant demand to replace the older and more used antibiotics.

Accordingly, a great many cephalosporin compounds have been synthesized and tested for appropriate antibiotic properties by those in the antibiotic field. Because of the above mentioned long felt need in this art for potent and effective antibiotics, even small improvements or advancements in the art can sometimes be very significant.

DESCRIPTION OF RELATED ART

A number of cephalosporin compounds having a double bond or catechol in the three position have been evaluated for antibiotic properties by those in the art; however, none teaches a combination of propenyl and di-hydroxyphenyl radicals as part of the C-3 side chain of cephalosporins with good antibaterical activity.

Patent documents and published patent applications which relate to cephalosporin compounds having a double bond and/or di-hydroxyphenyl moieties in the C-3 side chain are as follows:

(a) European Patent Application No. 30,630 (published Jun. 24, 1981) discloses a vast number of 7-acylamino-3-vinyl-chepalosporanic acid derivatives including, inter alia, those of the formula

[Structure: H₂N-thiazole-C(=N-O-A)-CONH-β-lactam-CH=CH₂, with CO₂H]

wherein A may be a lower alkyl group.

(b) U.S. Pat. No. 4,486,586 (issued Dec. 4, 1984 to Narita et al) and Japan Kokai 1-151586 (published Jun. 14, 1989) relate to, inter alia, cephalosporin derivatives of the formula

[Structure: H₂N-thiazole-S-C(=N-O-A)-CONH-β-lactam-CH=CH-CH₂-N⁺≡Q, with COO⁻]

wherein A is hydrogen, a straight or branched alkyl or cylcoalkyl group containing from 1 to 6 carbon atoms or a group of the formula $$-\underset{R^4}{\overset{R^3}{\underset{|}{\overset{|}{C}}}}-CO_2H$$

in which $R^3$ and $R^4$ are each independently hydrogen, methyl, or ethyl, or $R^3$ and $R^4$, taken together with the carbon atom to which they are atttached, may be a cycloalkylidene ring containing from 3 to 5 carbon atoms; and the group of the formula $$-\overset{\oplus}{N}\equiv Q$$

is a quaternary ammonio group.

(c) U.S. Pat. No. 4,751,295 (issued Jun. 14, 1988 to Oka et al) and European Application No. 329,785 (published Aug. 30, 1989) relate to, inter alia, cephalosporin derivatives of the formula

[Structure: H₂N-thiazole-S-N-C(=N-O-A)-CONH-β-lactam-CH=CH-CH₂-N⁺≡Q, with COOH]

wherein A is hydrogen, a straight or branched alkyl group containing from 1 to 4 carbon atoms or a group of the formula $$-\underset{R^4}{\overset{R^3}{\underset{|}{\overset{|}{C}}}}-CO_2H$$

in which $R^3$ and $R^4$ are each independently hydrogen, methyl, or ethyl, or $R^3$ and $R^4$ taken together with the carbon atom to which they are atttached, may be a cycloalkylidene ring containing from 3 to 5 carbon atoms; and the group of the formula $$-\overset{\oplus}{N}\equiv Q$$

is a quaternary ammonio group.

(d) European Patent Application 265,185 (published Apr. 27, 1988) discloses compounds of the formula

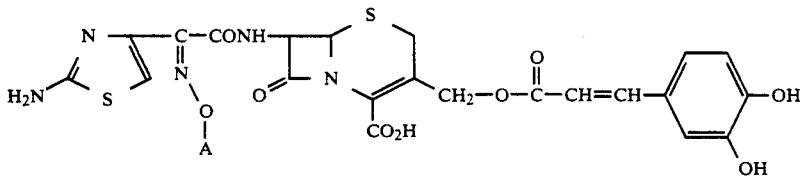

wherein A is a hydrogen, $C_{1-6}$ alkyl, $C_{3-6}$ cycloalkyl, carboxy $C_{1-6}$ alkyl.

(e) U.S. Pat. No. 4,874,856 (issued Oct. 27, 2989 to Iimura) relates to, inter alia, cephalosporins of the formula

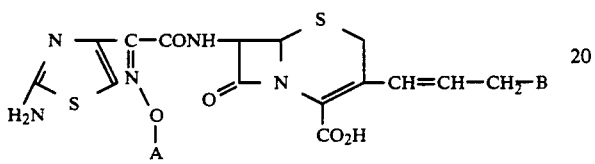

wherein A is a hydrogen, or an alkanoyl group having 2 to 4 carbon atoms; and B is hydrogen or a lower alkanoyloxy group having 2 to 3 carbon atoms.

(f) Japan Kokai 2-69484 (published Mar. 8, 1990)discloses, inter alia, cephalosporins of the formula

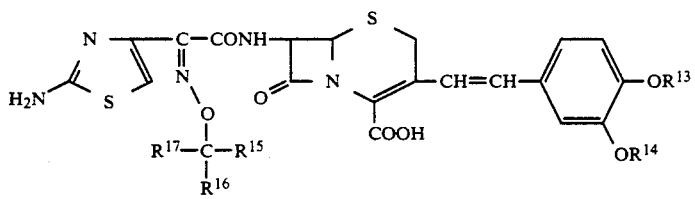

wherein $R^{15}$ is hydrogen or carboxy, $R^{16}$ and $R^{17}$ each are independently hydrogen or lower alkyl containing from 1 to 3 carbon atoms, and $R^{13}$ and $R^{14}$ each are independently hydrogen or acyl.

SUMMARY OF THE INVENTION

The present invention relates to new cephalosporins of the Formula

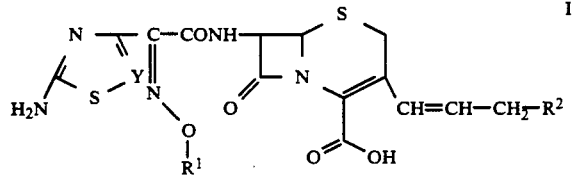

I wherein
Y is N or CH;
$R^1$ is hydrogen, a straight, branched, or cyclic lower alkyl group having up to six carbon atoms or a radical of the formula

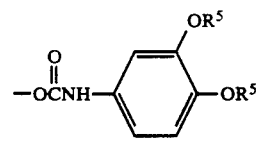

in which $R^3$ and $R^4$ are each independently hydrogen, methyl, or ethyl, or $R^3$ and $R^4$, taken together with the carbon atom to which they are attached, may be a cycloalkylidene ring containing from 3 to 5 carbon atoms;
$R^2$ is a radical selected from the group consisting of ![structure]

and

![structure]

in which $R^5$ is hydrogen or acetyl.

In another aspect, this invention relates to compounds of Formula I and their nontoxic pharmaceutically acceptable salts, physiologically hydrolyzable esters or solvates.

Representative compounds of this invention were selected for testing and were shown to display potent antibacterial activity. Thus, as another aspect of the invention, compounds of the series can be incorporated into pharmaceutical compositions for use in patients afflicted with bacterial infections.

DETAILED DESCRIPTION OF THE INVENTION

The present invention relates to new cephalosporins of the Formula

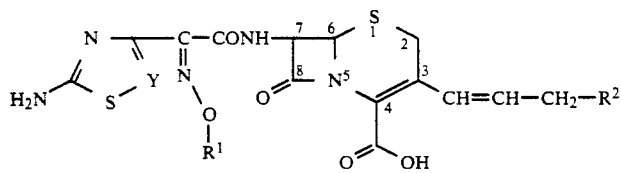

wherein
Y is N or CH;
R¹ is hydrogen, a straight, branched, or cyclic lower alkyl group having up to six carbon atoms or a radical of the formula

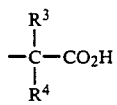

in which $R^3$ and $R^4$ are each independently hydrogen, methyl, or ethyl, or $R^3$ and $R^4$, taken together with the carbon atom to which they are attached, may be a cycloalkylidene ring containing from 3 to 5 carbon atoms;

$R^2$ is a radical selected from the group consisting of

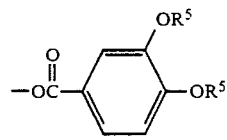

and

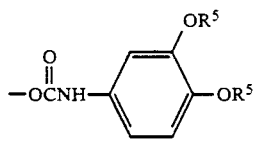

in which $R^5$ is hydrogen or acetyl.

As shown in the structural Formula I, the numbering system used for the cephalosphorins in this specification follows the most widely used system in the art.

The imino groups in the C-7 side chains of Formula I compounds have either the "syn" (Z) or "anti" (E) configuration. Formula I is drawn as the "syn" isomer. This invention comprises compounds of Formula I containing at least 90% of the "syn" isomer. Preferably the compounds of Formula I are "syn" isomers which are essentially free of the corresponding "anti" isomers.

In addition to the geometric isomerism possible with respect to the imino groups, the double bonds in the C-3 side chains of Formula I compounds and some intermediates thereof can exit as either in the "Z" (cis) or "E" (trans) configuration. The present invention includes compounds of Formula I with the double bonds in both the "Z" or "E" configurations.

The structural formulas as drawn herein are believed to be the ones which best represents the structures of the compounds. Some compounds within the scope of the Formula I may exit as other tautomeric forms, in which hydrogen atoms are transposed to other parts of the molecules and the chemical bonds between the atoms of the molecules are consequently rearranged. The structural Formula I is intended to represent and include such tautomeric forms, insofar as they may exits.

Also included within the scope of the invention are the nontoxic pharmaceutically acceptable salts, physiologically hydrolyzable esters or solvates of compounds of Formula I.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula I include $C_{1-6}$ alkyl, benzyl, 4-methoxybenzyl, indanyl, phthalidyl, methoxymethyl, $C_{1-6}$ alkanoyloxy($C_{1-6}$)alkyl, e.g. acetoxymethyl, pivaloyloxymethyl or propionyloxymethyl, $C_{1-6}$ alkoxycarbonyloxy($C_{1-6}$)alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)methyl and other physiologically hydrolyzable esters known and used in the penicillin and cephalosporin arts. Such esters are prepared by conventional techniques known in the art.

The pharmaceutically acceptable acid addition salts of Formula I compounds are those in which anion does not contribute significantly to the toxicity of the salt and are compatible with the customary pharmaceutical vehicles and adapted for oral or parenteral administration. The pharmeutically acceptable acid additions salts include the salts of compounds of Formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-tolenesulfonic acid and other acids known and used in the penicillin and cephalosporin arts. Preparation of these salts is carried out by conventional techniques involving reaction of compounds of Formula I with the acid in a substantially equivalent amount.

Compounds of Formula I also form pharmaceutically acceptable metal and amine salts in which the cation does not contribute significantly to the toxicity or biological activity of the salt. These salts are also part of the present invention. Suitable metal salts include the sodium, potassium, calcium, barium, zinc and aluminum salts. The sodium or potassium salts are preferred. Amine salts prepared from amines used, for instance, with benzyl penicillin which are capable of forming stable salts with the acidic carboxy group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine and dicyclohexylamine.

Compounds of Formula I exhibit high antibacterial activity against various Gram-positive and Gram-negative bacteria, and are useful in the treatment of bacterial infections in animals, including man. Compounds of Formula I may be formulated for parenteral use in a conventional manner utilizing known pharmaceutical carriers and excipients, and may be presented in unit dosage form or in multidosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. Compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of compounds of Formula I. The dosage of Formula I compounds is dependent on such factor as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

Compounds of Formula I wherein $R^2$ is a radical of the formula

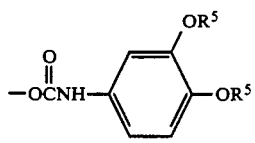

in which $R^5$ is as previously defined can be made by the method which comprises the steps described in Route A below or appropriate modification thereof.

Route A a) Replacing the chlorine atom in a compound of formula II with a hydroxy group to afford a compound of formula III. The conversion may be achieved with silver nitrate in wet DMSO.

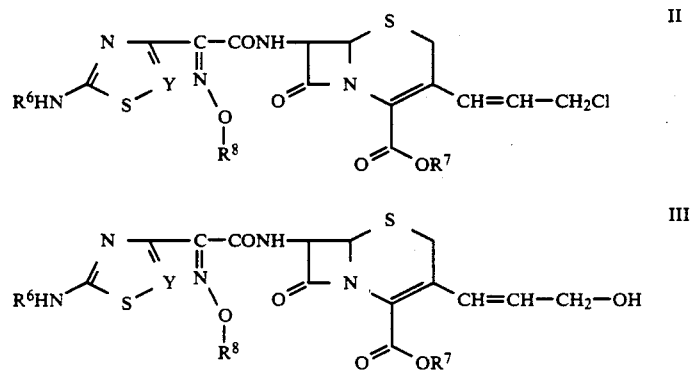

In the foregoing formulas, $R^6$ is an amino protecting group, preferably triphenylmethyl (trityl); $R^7$ is a carboxy protecting group, preferably diphenylmethyl (DPM). $R^8$ is hydrogen, a conventional hydroxy protecting group such as trityl group, a straight, branched, or cyclic lower alkyl group having up to six carbon atoms or a radical of the formula

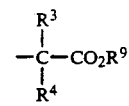

in which $R^3$ and $R^4$ are each independently hydrogen, methyl, or ethyl, or $R^3$ and $R^4$ taken together with the carbon atom to which they are attached, may be a cycloalkylidene ring containing from 3 to 5 carbon atoms; and $R^9$ is hydrogen or preferably a conventional carboxy protecting group such as DPM. Compounds of formula II can be made according to the processes or variations thereof described in the following patents:

U.S. Pat. No. 4,708,955 issued Nov. 24, 1987 to Iimura et al;

U.S. Pat. No. 4,751,295 issued Jun. 24, 1988 to Oka et al; and

U.S. Pat. No. 4,486,586 issued Dec. 4, 1984 to Narita et al.

b) Reacting isocyante IV with a compound of formula III to afford a compound of formula V.

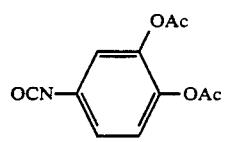

IV

-continued

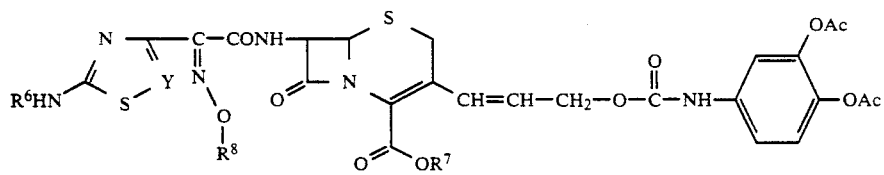

The synthesis of compound of formula IV is described in Japan Kokai 63-152389 (published Jun. 24, 1988).

c) Finally, removing the protecting group(s) in V to afford desired Formula I compounds.

Preparation of Formula I compounds wherein $R^2$ is a radical of the formula

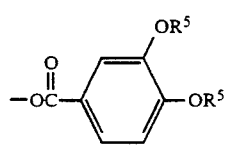

can be accomplished by the method comprising the steps described in Route B or appropriate modification thereof.

Route B a) Replacing the chlorine atom in VI with iodine to afford a compound of formula VII.

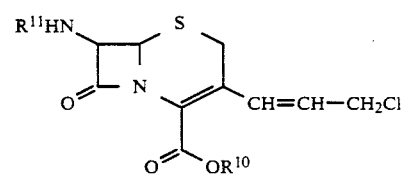

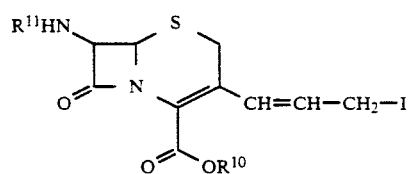

In the foregoing formulas, $R^{11}$ is an amino protecting group, preferably t-butoxycarbonyl; and $R^{10}$ is hydrogen or a conventional carboxy protecting group such as DPM. The conversion can be accomplished with sodium iodide in acetone.

b) Displacing the iodine atom in a compound of formula VII by acid VIII to afford a compound of formula IX.

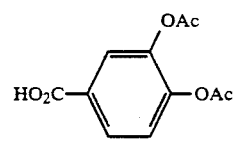

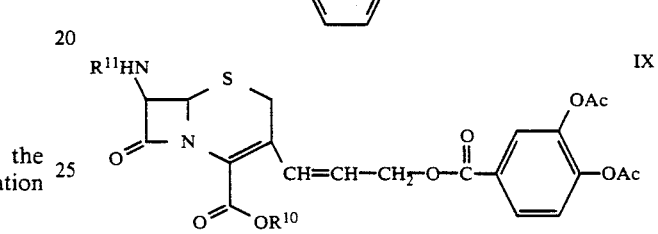

c) Deblocking the amino protecting group $R^{11}$ from a compound of formula IX to afford a compound of formula X. Depending on the nature of the protecting groups, their removal can e done by acid hydrolysis, enzymatic hydrolysis, and the like.

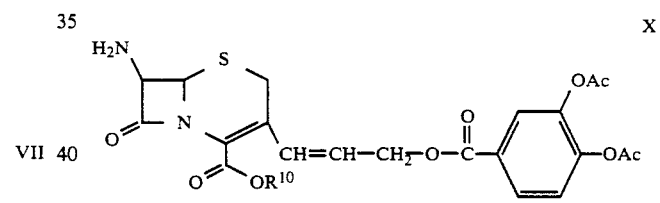

When $R^{11}$ is a t-butoxycarbonyl group, it can be removed with p-toluenesulfonic acid in wet acetonitrile.

d) Coupling a compound of formula X with an activated acid derivative XI to afford a compound of formula XII.

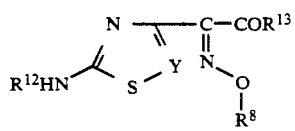

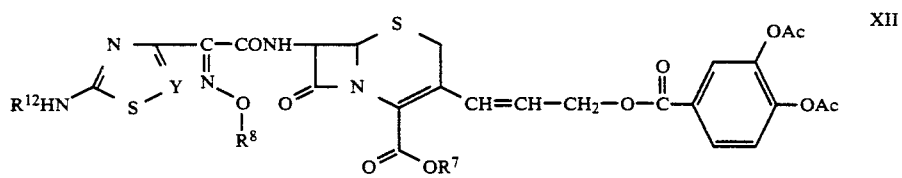

wherein $R^8$ is as previously defined; $R^{12}$ is hydrogen or an amino protecting group, preferably trityl; $R^{13}$ is a suitable leaving group such as chloro or 1-benzotriazolyloxy radical.

e) Removing the protecting group(s) from XII to afford desired compounds of Formula I. Depending of the nature of the protecting groups, their removal can be accomplished by acid hydrolysis, enzymatic hydrolysis, and the like.

DESCRIPTION OF SPECIFIC EMBODIMENTS

The specific examples and Schemes A and B which follow illustrate the synthesis of representative compounds of the instant invention, and are not to be contrued as limiting the invention in sphere or scope. The methods disclosed may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), quartet (q), doublet of doublet (dd), doublet of triplet (dt), and doublet of quartet (dq). The solvents employed for taking NMR spectra are DMSO-$d_6$ (perdeuterodimethysulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

EXAMPLE 1

Diphenylmethyl 7-t-butoxycarbonylamino-3-[(E)-3-iodo-1-propen-1-yl]-3-cephem-4-carboxylate (VIIa)

To an ice cooled solution of sodium iodide (900 mg, 6 mmol) in acetone was added a solution of diphenylmethyl 7-t-butoxycarbonylamino-3-[(Z)-3-chloro-1-propen-1-yl]-3-cephem-4-carboxylate (VIa) (1.08 g, 2 mmol) in acetone (2.5 ml). The mixture was stirred while being cooled in an ice bath for 3.5 hours, and was concentrated under reduced pressure. The residue was diluted with ethyl acetate and aqueous sodium thiosulfate solution. The organic layer was separated, dried over magnesium sulfate, and concentrated. 923mg of the title product was obtained as a yellow powder after crystallization from a small volume of ethanol (73% yield).

IR $\nu_{max}$(KBr) $cm^{-1}$ 1785, 1720, 1685, 1520; UV $\lambda_{max}$ ($CH_2Cl_2$) nm ($\epsilon$) 318 (19000); $^1H$ NMR ($CDCl_3$) $\delta$ 1.46(9H,s), 3.54(2H,s), 3.83(2H,d J=8 Hz), 4.96(1H,d J=4.5 Hz), 5.15(1H, J=9.5 Hz), 5.6 (1H,dd J=4.5 & 9.5 Hz), 6.06 (1H,dt J=16 & 8 Hz), 6.82 (1H, d, J=16 Hz), 6.98 (1H,s), 7.33(10H, s).

EXAMPLE 2

Diphenylmethyl 7-t-butoxycarbonylamino-3-[(E)-3-(3,4-diacetoxybenzoyloxy)-1-propen-1-yl]-3-cephem-4-carboxylate (IXa)

A mixture of 3,4-diacetoxybenzoic acid (VIII) (240 mg, 1 mmol) and cesium carbonate (160 mg, 0.49 mmol) in DMF(3 ml) was stirred at room temperature overnight to afford a clear solution. To the chilled solution was added the iodopropenyl cephem VIIa (600 mg, 0.95 mmol). The mixture was stirred for 30 min under cooling and diluted with ethyl acetate and aqueous sodium thiosulfate. The organic layer was washed with brine, dried over magnesium sulfate, and concentrated under reduced pressure to afford 815 mg of an amorphous powder, which was then subjected to column chromatography [Keisel gel 60, 20 g], using toluene-ethyl acetate (10/1) as an eluent to obtain 536 mg of the title product (76% yield).

IR $\nu_{max}$(KBr) $cm^{-1}$ 1775, 1710, 1520, 1490; $^1H$ NMR ($CDCl_3$) $\delta$ 1.45(9H,s), 2.27(6H,s), 3.55(2H,s), 4.46(2H,d J=6.5 Hz), 4.96(1H,d J=4.5 Hz), 5.15(1H,d J=10 Hz), 5.58 (1H,dd J=4.5 & 10 Hz), 6.00(1H,dt J=16 & 6.5 Hz), 6.95(1H,d J=16 Hz), 6.96(1H,s), 7.28(11H,br s), 7.8–7.95(2H,m).

EXAMPLE 3

Diphenylmethyl 7-amino-3-[(E)-3-(3,4-diacetoxybenzoyloxy)-1-propen-1-yl]-3-cephem-4-carboxylate (Xa)

To a warm solution of compound of formula IXa (500 mg, 0.67 mmol) in acetonitrile (10 ml) was added a solution of p-toluenesulfonic acid hydrate (260 mg, 1.37 mmol) in acetonitrile (10 ml). The mixture was stirred at 50° C. for an hour, and then concentrated in vacuo. The residue was diluted with ethyl acetate, and washed with aqueous sodium bicarbonate and brine, and dried over magnesium sulfate. The solvent was removed in vacuo to obtain 376 mg of compound of formula Xa (87% yield).

IR $\nu_{max}$ (film) $cm^{-1}$ 1770, 1720, 1200; $^1H$ NMR ($CDCl_3$) $\delta$ 2.30(6H,s), 3.55(2H,br s), 4.69(2H,d J=5.6 Hz), 4.76(1H,d J=4.5 Hz), 4.95(1H,d J=4.5 Hz), 5.97(1H,dt J=16 & 5.6 Hz), 6.88(1H,d J=16 Hz), 7.00(1H,s), 7.3(11H,m), 7.8–7.95(2H,m).

EXAMPLE 4

Diphenylmethyl 7-[(Z)-2-(2-aminothiazol-4-yl)-2-methoxyiminoacetamido]-3-[(E)-3-(3,4-diacetoxybenzoyloxy)-1-propen-1-yl]-3-cephem-4-carboxylate (XIIa)

To a stirred solution of compound of formula Xa (370 mg, 0.57 mmol) in THF (2.5 ml) was added 1-benzotriazolyl (Z)-2-(2-aminothiazol-4-yl)-2-methoxyiminoacetate (200 mg, 0.63 mmol). The mixture was stirred at room temperature for 1.5 hours, and concentrated in vacuo. The residue was subjected to column chromatography [Kiesel gel 60, 30 g] using chloroform-methanol(30/1) as eluent to afford 308 mg of the title compound (65% yield).

IR $\nu_{max}$(KBr) $cm^{-1}$ 1770, 1715, 1670, 1530, 1200; $^1H$ NMR ($CDCl_3$) $\delta$ 2.27(6H,s), 3.55(2H,br s), 4.0(3H,s), 4.69(2H,d J=6.5 Hz), 5.06(1H,d J=4.5 Hz), 5.8–6.2(3H,m), 6.80(1H,s), 6.95(1H,s), 6.96(1H,d J=16 Hz), 7.28(11H,m), 7.75–7.95(2H,m).

EXAMPLE 5

7-[(Z)-2-(2-Aminothiazol-4-yl)-2-methoxyiminoacetamido]-3-[(E)-3-(3,4-dihydroxybenzoyloxy)-1-propen-1-yl]-3-cephem-4-carboxylic acid (Ia)

To an ice cooled mixture of compound of formula XIIa (300 mg, 0.36 mmol) in methylene chloride (1.5 ml) and anisole (1 ml) was added trifluoroacetic acid(4 ml). The mixture was left at room temperature for an hour, and concentrated under reduced pressure. The residue was triturated with isopropyl ether (30 ml), and the solid was collected by filtration to afford 258 mg of a pale yellow powder, which was subsequently dissolved in a phosphate buffer (pH7.0, 0.33M, 25 ml). The buffered solution was treated with acetylesterase (SIGMA, 1.5 ml) and the pH of the mixture was maintained between 6.8 and 7.2 by sodium bicarbonate and citric acid. After the reaction had reached completion (as determined by HPLC), the mixture was acidified to pH 2 by 2N hydrochloric acid, and adsorbed on a column of Diaion HP-20(40 ml). The column was eluted with water and then with 50% methanol. The eluate was monitored by UV(254 nm). The desired fractions were combined and concentrated to give 98 mg of a pale yellow powder, which was further purified as follows. The crude product (90 mg) was dissolved in water, containing sodium bicarbonate (20 mg, 0.24 mmole), and the resultant solution was adsorbed onto a column of Preparative C-18 125° A(Waters, 60 ml) and eluted with water, followed by 10% and 15% aqueous methanol. The eluate was continuously monitored by UV (254 nm). The desired fractions were combined and concentrated to half of their original volume. The resultant solution was acidified with 2N hydrochloric acid, and passed through a column of HP-20(30 ml). The column was eluted with water and then with 50% methanol, and the desired fraction was concentrated to obtain 47 mg of compound of formula Ia as a pale yellow powder (23% yeild), mp>163° C. (dec.).

IR $\nu_{max}$(KBr) cm$^{-1}$ 1760, 1670, 1600, 1520; UV $\lambda_{max}$ (pH 7 buffer) nm ($\epsilon$) 222(24000), 265(shoulder, 21600), 294(28500); $^1$H NMR (D$_2$O) $\delta$ 3.69(2H,ABq), 4.00(3H,s), 5.26 (1H,d J=4.5Hz), 5.82(1H,d J=4.5 Hz), 6.09(1H,dt J=16 & 5.9 Hz), 6.86(1H,d J=16 Hz), 6.96(1H,d J=8.4 Hz), 7.03(1H,s), 7.5-7.55(2H,m); MS-FAB m/z 576(M+H)$^+$, 598(M+Na)$^+$.

EXAMPLE 6

Diphenylmethyl 7-[(Z)-2-(5-amino-1,2,4-thiadiazol-3-yl)-2methoxyiminoacetamido]-3-[(E)-3-(3,4-diacetoxybenzoyloxy)-1-propen-1-yl]-3-cephem-4-carboxylate (XIIb)

Using a smilar procedure to obtain compound of formula XIIa, the 7-aminocephem Xa was N-acylated with benzotriazol-1-yl 2-[(Z)-5-amino-1,2,4-thiadiazol-3-yl]-2-methoxyiminoacetate to afford 323 mg of the title product (78% yield).

IR $\nu_{max}$(KBr) cm$^{-1}$ 1770, 1715, 1680, 1520, 1200; $^1$H NMR (CDCl$_3$) $\delta$ 2.26(6H,s), 3.55(2H,br s), 4.07(3H,s), 4.68(2H,d J=6.4 Hz), 5.09(1H,d J=4.5 Hz), 5.8-6.2(3H,m), 6.94(1H,s), 6.98(1H,d J=16 Hz), 7.26(11H,m), 7.75-7.9(2H,m).

EXAMPLE 7

7-[(Z)-2-(5-Amino-1,2,4-thiadiazol-3-yl)-2-methoxyiminoacetamido]-3-[(E)-3-(3,4-dihydroxybenzoyloxy)-1-propen-1-yl]-3-cephem-4carboxylic acid (Ib)

The removal of the protecting groups and purification of compound of formula XIIb (310 mg, 0.37 mmole) was carried out in a manner similar to the method described in Example 5 to afford 80 mg of the title product as a pale yellow powder (37.5% yield), mp.>155° C.(dec.).

IR $\nu_{max}$(KBr) cm$^{-1}$ 1760, 1660, 1600, 1520; UV $\lambda_{max}$ (pH 7 buffer) nm ($\epsilon$) 221(24500), 293(25500); $^1$H NMR (D$_2$O) $\delta$3.70 (2H, ABq), 4.10(3H,s),5.27(1H,d J=4.5 Hz), 5.85(1H,d J=4.5 Hz), 6.10(2H,dt J=16 & 5.9 Hz), 6.85(1H,d J=16 ), 6.93(1H,d J=8 Hz), 7.5-7.56 (2H,m); MS-FAB m/z 577(M+H)$^+$, 599(M+Na)$^+$.

EXAMPLE 8

Diphenylmethyl 7-[(Z)-2-(2-tritylaminothiazol-4-yl)-2-(1-t-butoxycarbonyl-1-methylethoxyimino)acetamido]-3-[(E)-3-(3,4-diacetoxybenzoyloxy)-1-propen-1-yl]-3-cephem-4-carboxylate (XIIc)

To a cooled solution of (Z)-2-(2-tritylaminothiazol-4-yl)-2-(1-t-butoxycarbonyl-1-methylethoxyimino)acetic acid (300 mg, 0.5 mmol) in methylene chloride (3 ml) was added phosphorous pentachloride (104 mg, 0.5 mmol) at −10° C. The mixture was stirred under cooling for 30 min, and the resulting clear solution was transferred into a stirred solution of compound of formula Xa (300 mg, 0.47 mmol) and N,O-bis(trimethylsilyl)acetamide (0.2 ml, 0.8 mmol) in methylene chloride (5 ml) under cooling at −10° C. The mixture was stirred for 30 min at −10° C., and for additional 30 min at 0° C., and then poured into a stirred mixture of ethyl acetate (50 ml) and 6% aqueous sodium bicarbonate (50 ml). The organic layer was washed with brine, dried over magnesium sulfate, and concentrated under reduced pressure to obtain 613 mg of the crude product, which was purified by column chromatography [Kiesel gel 60, 20 g]. The column was eluted with toluene-ethyl acetate (5/1) (monitored by TLC), and the desired fractions were combined and concentrated to give 312 mg of compound of formula XIIc (56% yield).

IR $\nu_{max}$(KBr) cm$^{-1}$ 1775, 1715, 1680, 1520, 1200; $^1$H NMR (CDCl$_3$) $\delta$ 1.40(9H,s), 1.57(3H,s), 1.60(3H,s), 2.28(6H,s), 3.53(2H,br s), 4.72(2H,d J=5.6 Hz), 5.05(1H,d J=4.5 Hz), 5.8-6.2(3H,m), 6.69(1H,s), 6.96(1H,s), 6.98(1H,d J=16 Hz), 7.3(26H,m), 7.8-7.95(2H,m).

EXAMPLE 9

7-[(Z)-2-(2-Aminothiazol-4-yl)-2-(1-carboxy-1-methylethoxyimino)acetamido]-3-[(E)-3-(3,4-dihydroxybenzoyloxy)-1-propen-1yl]-3-cephem-4-carboxylic acid (Ic)

The removal of the protecting groups and purification of compound of formula XIIc (310 mg, 0.26 mmole) was carried out in a manner similar to the method described in Example 5 to afford 76 mg of the title product as a pale yellow powder (45% yield), mp.>163° C.(dec.).

IR $\nu_{max}$(KBr) cm$^{-1}$ 1760, 1670, 1280; UV $\lambda_{max}$ (pH 7 buffer) nm ($\epsilon$) 218(shoulder 26200), 260(shoulder 22000), 293(28500); $^1$H NMR (D$_2$O) $\delta$ 1.53(3H,s), 1.54(3H,s), 3.72(2H,ABq), 5.29(1H,d J=4.8 Hz), 5.85(1H,d J=4.8 Hz), 6.13(1H,dt J=16 & 5.9 Hz), 6.89(1H,d J=16 Hz), 7.01(1H,d J=8.4 Hz), 7.04(1H,s), 7.56-7.6(2H,m); MS-FAB m/z 648(M+H)$^+$, 670(M+Na)$^+$.

EXAMPLE 10

Diphenylmethyl 7-[(Z)-2-(2-aminothiazol-4yl)-2-trityloxyiminoacetamido]-3-[(E)-3-(3,4-diacetoxybenzoyloxy)-1-propen-1-yl]-3-cephem-4-carboxylate (XIId)

To a solution of diphenylmethyl 7-amino-3-[(E)-3-(3,4-diacetoxybenzoyloxy)-1-propen-1-yl]-3-cephem-4-carboxylate (Xa) (376 mg, 0.59 mmol) in DMF (4 ml) was added benzotriazol-1-yl-2-(2-aminothiazol-4-yl)-2-trityloxyimino acetate (345 mg, 0.63 mmol) and the mixture was stirred for 3 hours at room temperature.

The reaction mixture was diluted with EtOAc, washed with water, dried over anhydrous $MgSO_4$ and concentrated under reduced pressure. The residue was chromatographed on a column of silica gel to give 422 mg of the title compound (68% yield).

IR $\nu_{max}$ (KBr) cm$^{-1}$ 3440, 1775, 1715, 1680, 1620; NMR δ (CDCl$_3$), 1.55 (2H, br s), 2.29 (6H, s), 3.44 (2H, br s), 4.73 (2H, d), 5.03 (1H, d, j=5 Hz), 5.94 (1H, dd, J=5 & 8 Hz), 6.60 (1H, s), 6.96 (1H, s), 6.8–7.6 (25H, m).

EXAMPLE 11

7-[(Z)-2-(2-Aminothiazol-4-yl)-2-hydroxyiminoacetamido]-3-[(E)-3l-(3,4-dihydroxybenzoyloxy)-1-propen-1-yl]-3-cephem-4-carboxylic acid (Id)

A mixture of diphenylmethyl 7-[(Z)-2-(2-aminothiazol-4-yl)-2-trityloxyiminoacetamido]-3-[(E)-3,4-diacetoxybenzoyloxy)-1-propen-1-yl]-3-cephem-4-carboxylate (XIId) (420 mg, 0.40 mmol), TFA (4 ml), anisole (0.4 ml) and CH$_2$Cl$_2$ (1 ml) was stirred for 1 hour at room temperature. The reaction mixture was concentrated under reduce pressure and the residue was triturated with isopropyl ether to afford 293 mg of partially deprotected product still having diacetoxybenzoyl group as a TFA salt.

IR; $\nu_{max}$ (KBr) cm$^{-1}$ 1765, 1710, 1670.

The TFA salt (290 mg) was dissolved in pH 7 buffer (29 ml) and treated with acetylesterase (1 ml). The mixture was stirred for 4 hours at room temperature while maintaining the pH 7 of the solution by adding aqueous NaHCO$_3$. The reaction mixture was acidified with 4N HCl and chromatographed on a column of HP-20. The desired fractions were combined and concentrated under reduced pressure to afford 119 mg of the title compound (54% yield), mp 153° C. (dec).

MS-FAB m/z 562 [M+H]$^+$; IR $\nu_{max}$ (KBr) cm$^{-1}$ 3400, 2900, 1765, 1670; UV $\lambda_{max}$ (pH 7 buffer) nm (ε) 220 (24100), 267 (shoulder, 19500), 293 (25800) NMR; δ (D$_2$O+NaHCO$_3$) 3.66 & 3.72 (2H, ABq, J=17 Hz), 5.27 (1H,d, J=5 Hz), 5.84 (1H,d, J=5 Hz), 6.09 (1H, dt, J=6 & 16 Hz), 6.85 (1H, d, J=16 Hz), 6.88 (1H, d, J=9 Hz), 7.00 (1H, s), 7.48 (1H, d, J=2 Hz), 7.52 (1H, dd, J=2 & 9 Hz).

EXAMPLE 12

Diphenylmethyl 7-[2-(2-tritylaminothiazol-4yl)-2-methoxyiminoacetamido]-3-[(E)-3-hydroxypropen-1-yl]-3-cephem-4-carboxylate (IIIa)

To a mixture of diphenylmethyl 7-[2-(2-tritylaminothia-zol-4-yl)-2-methoxyiminoacetamido]-3-[(Z)-3-chloropropen-1-yl]-3-cephem-4-carboxylate (IIa) (715 mg, 0.825 mmol) in DMSO (9 ml) and water (2.5 ml) was added silver nitrate (700 mg) under cooling and the mixture was stirred for 6 hours at room temperature. The mixture was poured into water (50 ml) and extracted with CHCl$_3$ (300 ml). The organic phase was washed with water and concentrated under reduced pressure. The residue was chromatographed on a column of silica gel (Merck kieselgel 60, 20 g) by successively eluting with 0.5% MeOH/CHCl$_3$, 1% MeOH/CHCl$_3$ and 3% MeOH/CHCl$_3$. The eluate was monitored by TLC and the fractions containing the desired product were combined. Evaporation under reduced pressure gave 452 mg (65% yield) of the title product as an amorphous powder.

IR $\nu_{max}$(KBr) cm$^{-1}$ 1770, 1710, 1660, 1510; MS-FAB m/z 848 [M+H]$^+$; $^1$H NMR (CDCl$_3$) δ 3.52 (1H, d, J=18 Hz), 3.61 (1H, d, J=18 Hz), 4.07 (3H, s), 4.15 (2H, m), 5.08 (1H, d, J=5 Hz), 5.92 (1H, dd, J=5 and 9 Hz), 6.05 (1H, dt, J=6 and 16 Hz), 6.76 (1H, s), 6.89 (1H, d, J=9 Hz), 6.93 (1H, d, J=16 Hz), 6.99 (1H, s), 7.23–7.45 (25H, m).

EXAMPLE 13

Diphenylmethyl 7-[2-(2-tritylaminothiazol-4-yl)-2-methoxyiminoacetamido]-3-[(E)-3-(N-3,4-diacetoxyphenyl)-carbamoyloxy-1-propen-1-yl]-3-cephem-4-carboxylate (Va)

3,4-Diacetoxyphenyl isocyanate (5.3 mmol; for the prepartion of this compound see: Japan Kokai 63-152389, published 6/24/88) was added to a solution of compound of formula IIIa (452 mg) in DMF (1 ml) and the resulting mixture was stirred for 3 hours at room temperature. The mixture was poured into water (20 ml) and extracted with EtOAc (300 ml). The extracts were washed with water and chromatographed on a column of silica gel (Merck kieselgel 60, 20 g) by eluting with CHCl$_3$. The eluate was monitored by TLC and the desired fractions were combined. Concentration of the combined fractions under reduced pressure gave 415 mg (72% yield) of the title product as an amorphous powder.

IR $\nu_{max}$(KBr) cm$^{-1}$ 1765, 1720, 1520; MS-FAB m/z 1083 [M+H]$^+$; $^1$H NMR (CDCl$_3$) δ 2.27(3H, s), 2.28(3H, s), 3.54 (1H, d, J=18 Hz), 3.62 (1H, D, J=18 Hz), 4.07 (3H, s), 4.64 (2H, m), 5.09 (1H, d, J=5 Hz), 5.94 (1H, dd, J=5 and 9 Hz), 6.01 (1H, dt, J=6 and 18 Hz), 6.60 (1H, s), 6.75 (1H, s), 6.81 (1H, d, J=9 Hz), 6.99 (1H, d, J=16 Hz), 6.99 (1H, s), 7.23–7.45(25H, m).

EXAMPLE 14

7-[(Z)-2-(2-Aminothiazol-4-Yl)-2-methoxyiminoacetamido]-3-[(E)-3-(N-3,4-dihyroxyphenyl)carbamoyloxy-1-propen-1-yl]-3-cephem-4-carboxylic acid (Ie)

A mixture of compound of formula Va (400 mg, 0.37 mmol) and anisole (2 ml) in TFA (3 ml) was stirred for 1 hour at room temperature. The mixture was diluted with isopropyl ether to precipitate the diacetoxyphenyl derivative of the title product (108 mg), which was collected by filtration. To a solution of the above product in pH 7 (0.33 M) phosphate buffer (10 ml) was added 0.8 ml of acetylesterase (Sigma) and the solution was maintained at pH 7 by addition of NaHCO$_3$ or citric acid for 0.5 hour at room temperature. The mixture was acidified to pH 2 by addition of conc. HCl and chromatographed on a column of HP-20 (20 ml). The column was eluted with water and then MeOH. The methanolic fraction was concentrated in vacuo, the residue was chromatographed on a column of Bondapak C$_{18}$ (20×300 mm) and the column was eluted successively with 2.5% MeCN/H$_2$O, 5% MeCN/H$_2$O and 12% MeCN/H$_2$O. The eluate was monitored by UV absorption at 254 nm and the fractions showing UV absorption were further checked by HPLC. The fractions containing the desired product were combined and concentrated in vacuo. The concentrate was freeze-dried to give 31 mg (14%) of the title product, mp 150° C. (dec.).

IR $\nu_{max}$(KBr) cm$^{-1}$ 1760, 1660, 1520; MS-FAB m/z 591[M+H]$^+$; UV $\lambda_{max}$ (pH 7 phosphate buffer) nm (ε) 236 (19800), 291 (24000); $^1$H NMR (D$_2$O+NaHCO$_3$) δ 3.66 (1H, d, J=18 Hz), 3.72 (1H, d, J=18 Hz), 4.00 (3H, s), 4.80 (2H, m), 5.26 (1H, d, J=5 Hz), 5.82 (1H, d, J=5

Hz), 6.03 (1H, dt, J=5 and 16 Hz), 6.78 (1H, d, J=16 Hz), 6.79 (1H, dd, J=2 and 9 Hz), 6.89 (1H, d, J=9 Hz), 6.97 (1H, d, J=2 Hz), 7.04 (1H, s).
SCHEME A
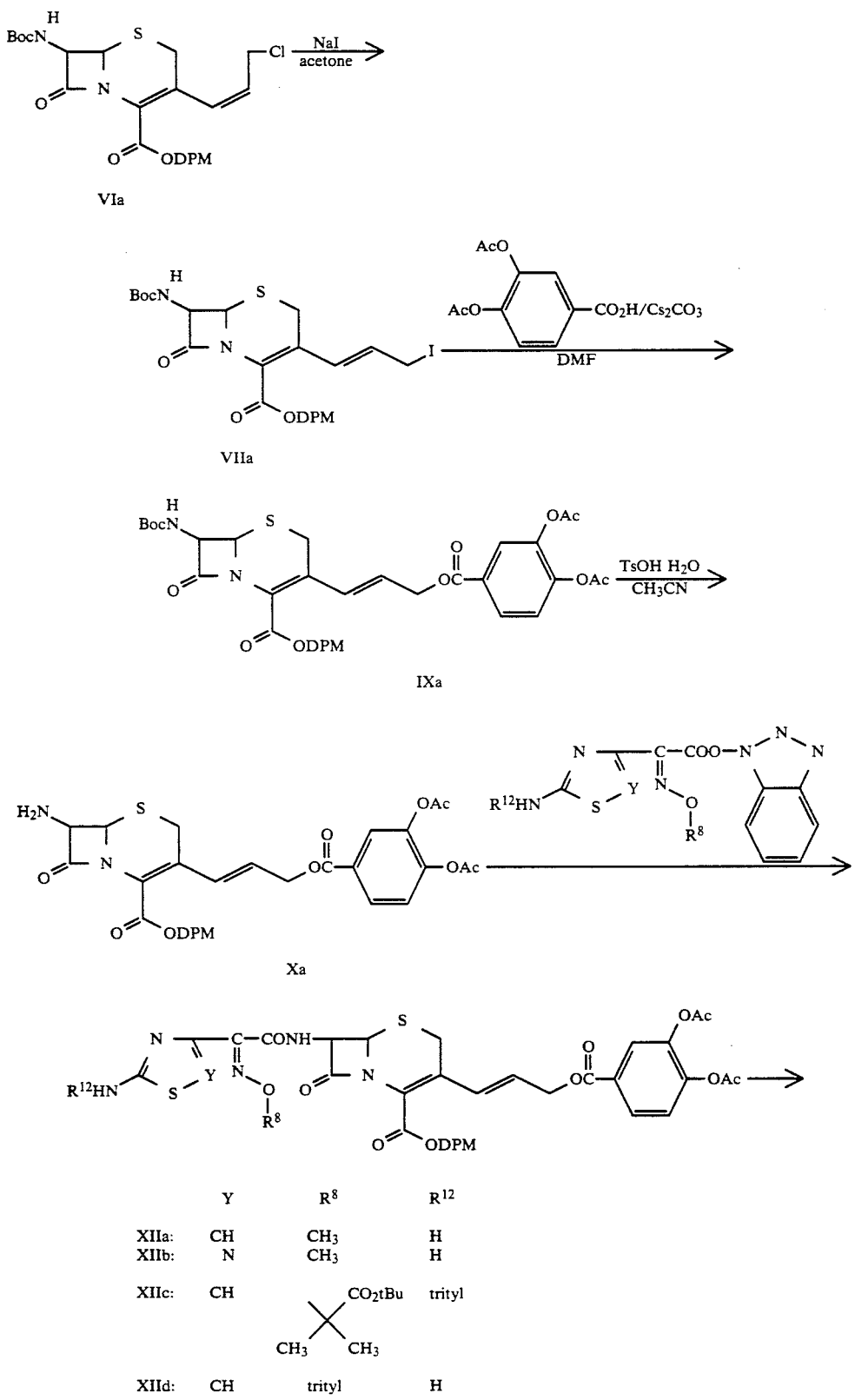

-continued
SCHEME A

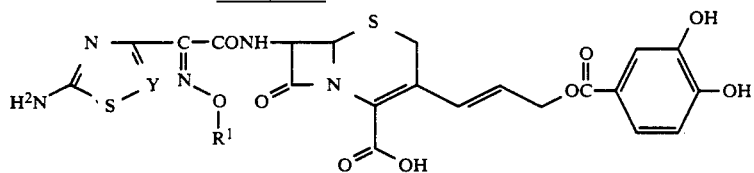

|     | Y  | R¹  |
|-----|----|-----|
| Ia: | CH | CH₃ |
| Ib: | N  | CH₃ |
| Ic: | CH | (CH₃)₂C(CO₂H) |
| Id: | CH | H   |

SCHEME B

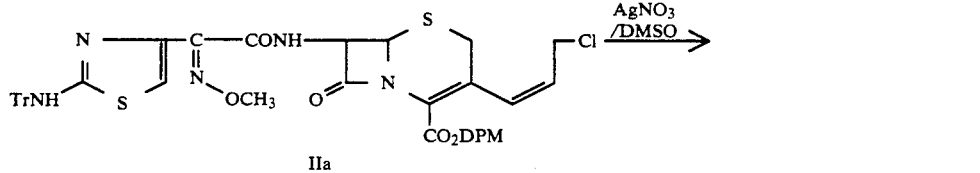
IIa

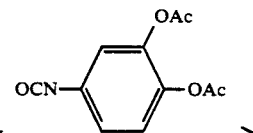

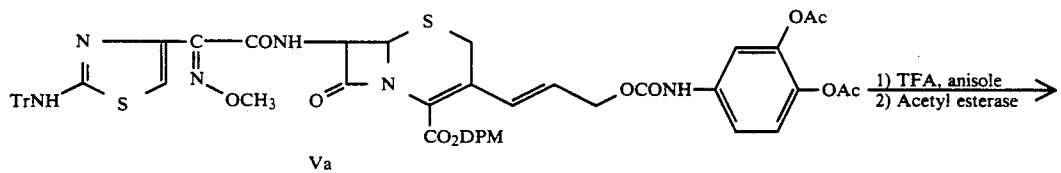
IIIa

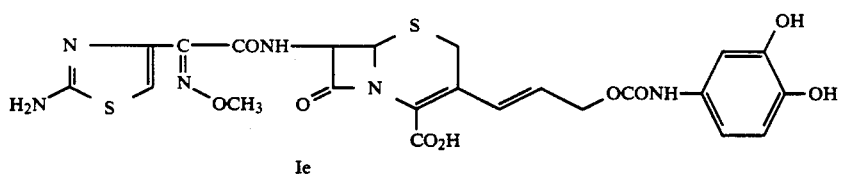
Va

Ie

Biological Data

For a primary evaluation of some representative compounds of this invention, minimum inhibitory concentrations (MIC's) were determined against 32 strains of test organisms by two-fold serial agar dilution method in Mueller-Hinton agar. Table 1 shows the geometric means of MICs in six groups of the test organisms.

In vivo antibacterial activity of this series of cephalosporins was determined against three bacterial infections, *S. aureus* Smith, *E. coli* Juhl and *P. aeruginosa* A9843A by intramuscular administration to mice just after the bacterial change. Table 2 shows $PD_{50}$ values of compounds Ia, Ib, and Ic against the three infections in comparison with the MIC values against the corresponding organisms.

Table 3 shows in vitro activity of compounds of formulas Ia and Id.

In vitro activity against anaerobic bacteria was determined on eight strains of *B. fragilis* by two-fold serial agar dilution method in GAM agar. Table 4 shows MIC values of compounds of formulas Ia, Ib, Ic and e.

TABLE 1

In vitro activity

| Compound | GP-Ia (5 strains) | Gp-Ib (5) | Gn-Ia (5) | Gn-Ib (5) | Gn-II (5) | Gn-III (7) |
|---|---|---|---|---|---|---|
| Ia | 1.2 | 1.6 | 0.017 | 0.029 | 0.46 | 1.9 |
| Ib | 3.4 | 3.1 | 0.022 | 0.026 | 0.53 | 0.49 |
| Ic | 8.3 | 13 | 0.022 | 0.019 | 0.17 | 0.82 |
| Ie | 6.3 | 7.2 | 0.23 | 0.46 | 3.6 | 50 |

Gp-Ia: Penicillin (PC)-sensitive *S. aureus*
Gp-Ib: PC-resistant *S. aureus*
Gn-Ia: Cephalothin (CET)-sensitive *E. coli*(2)*, *Kl. pneumoniae*(1) and *Pr. mirabilis*(2)
Gn-Ib: CET-resistant *E. coli*(3), and *Kl. pneumoniae*(2)
Gn-II: *M. morganii*(1), *Ent. cloacae*(2), and *Ser. marcescens*(2)
Gn-III: *Ps. aeruginosa* (7)
*a number in the bracket shows the number of strains used

TABLE 2

In vivo efficacy

| Compound | S. aureus Smith MIC (μg/ml) | S. aureus Smith PD$_{50}$ (mg/kg) | E. coli Juhl MIC (μg/ml) | E. coli Juhl PD$_{50}$ (mg/kg) | P. aeruginosa 9843A MIC (μg/ml) | P. aeruginosa 9843A PD$_{50}$ (mg/kg) |
|---|---|---|---|---|---|---|
| Ia | 1.6 | 0.4 | 0.1 | 0.05 | 3.1 | 0.62 |
| Ib | 3.1 | 0.68 | 0.1 | 0.037 | 0.4 | 0.17 |
| Ic | 12.5 | 2.2 | 0.2 | 0.062 | 0.2 | 0.25 |

TABLE 3

In Vitro activity of compounds Id and Ia

| Organisms | | MIC (μg/mL) Id | MIC (μg/mL) Ia |
|---|---|---|---|
| S. aureus | 209P | 0.8 | 3.1 |
| " | Smith | 0.8 | 1.6 |
| " | 4-1015 (MRSA) | 6.3 | 12.5 |
| " | IPM-24 (MRSA) | 100 | >100 |
| S. epidermidis | 11-1168 | 3.1 | 3.1 |
| " | 11-1230 | 6.3 | 3.1 |
| E. faecalis | A9808 | 12.5 | 100 |
| E. faecium | A24817 | 100 | >100 |
| M. luteus | 1001 | 0.2 | 0.1 |
| B. subtilis | PCI 219 | 0.4 | 0.2 |
| E. coli | Juhl A15119 | 0.2 | 0.05 |
| E. coli | 255 | 0.8 | 0.2 |
| K. pneumoniae | PCI 602 | 0.025 | <0.0063 |
| P. mirabilis | IFO-2849 | 0.2 | 0.05 |
| P. vulgaris | IPM-13 | >100 | >100 |
| M. morgani | 1510 | 6.3 | 3.1 |
| " | 1510/9 | 0.2 | 0.05 |
| P. rettgeri | IPM-14 | 0.4 | 0.05 |
| E. cloacae | IPM-12 | >100 | >100 |
| S. marcescens | IPM-15 | >100 | >100 |
| " | IPM-16 | >100 | >100 |
| C. freundii | GN 7391 | 50 | 12.5 |
| P. aeruginosa | A9843A | >100 | 3.1 |
| " | A20599 | >100 | 3.1 |
| " | KKA 19 | >100 | 50 |
| " | IPM-8 | >100 | 6.3 |
| " | IPM-9 | >100 | 6.3 |
| X. maltophilia | GN 12873 | >100 | 50 |
| " | No. 661 | >100 | 12.5 |
| P. cepacia | No. 651 | >100 | 12.5 |
| " | A21213 | >100 | >100 |
| C. terrigena | IFO 12685 | 0.8 | 0.8 |

Medium: Mueller-Hinton agar (pH = 7.2)
Incubation temperature: 32° C. 18 hr.
Inoculum size: 10$^6$ cells/ml

TABLE 4

In Vitro activity of compound Ie against anaerobes

| Organism | Ie | Ia | Ib | Ic |
|---|---|---|---|---|
| [Gn: Beta-Lactamase(−)] | | | | |
| B. fragilis A 22693 | 3.1 | 0.8 | 3.1 | 3.1 |
| B. fragilis A 22053 | 3.1 | 0.8 | 3.1 | 0.8 |
| B. fragilis A 22021 | 0.4 | 0.2 | 0.2 | 0.2 |
| B. fragilis A 21916 | 6.3 | 1.6 | 12.5 | 0.8 |
| [Gn: Beta-Lactamase(+)] | | | | |
| B. fragilis A 22534 | >100 | >50 | >50 | >100 |
| B. fragilis A 22695 | 25 | 12.5 | 25 | 3.1 |
| B. fragilis A 22533 | >100 | >50 | >50 | >100 |
| B. fragilis CUH-108* | 100 | 25 | >50 | 12.5 |
| [Gp] | | | | |
| C. difficile A 21675* | 50 | 12.5 | 25 | 50 |
| C. perfringens A9635 | 1.6 | 0.2 | 0.4 | 0.4 |
| P. acnes A 21933 | 1.6 | 0.4 | 0.8 | 0.8 |

*Clindamycin-resistant

What is claimed is:
1. A compound of the formula wherein
Y is N or CH;
R$^1$ is hydrogen, a straight, branched, or cyclic lower alkyl group having up to six carbon atoms or a radical of the formula in which R$^3$ and R$^4$ are each independently hydrogen, methyl, or ethyl, or R$^3$ and R$^4$, taken together with the carbon atom to which they are attached, may be a cycloalkylidene ring containing from 3 to 5 carbon atoms;
R$^2$ is a radical selected from the group consisting of and -continued

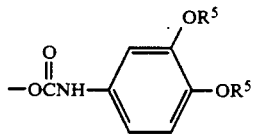

wherein $R^5$ is hydrogen or acetyl;
or a nontoxic pharmaceutically acceptable salt, physiologically hydrolyzable ester or solvate thereof.

2. A compound of claim 1 having the formula

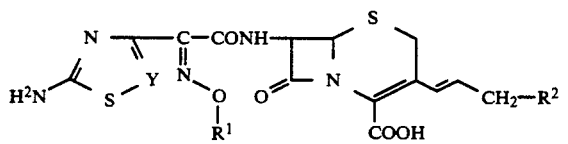

in which Y is CH and the double bond in the C-3 side chain is in the E configuration.

3. A compound of claim 1 having the formula

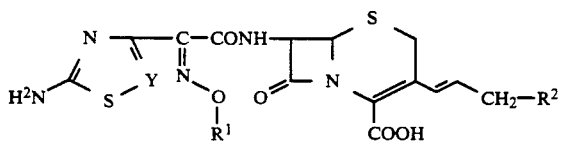

in which Y is N and the double bond in the C-3 side chain is in the E configuration.

4. A compound of claim 2 in which $R^2$ equals the radical of the formula

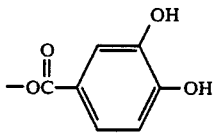

5. The compound of claim 4 in which $R^1$ equals $C(CH_3)_2CO_2H$.

6. The compound of claim 4 in which $R^1$ equals methyl.

7. The compound of claim 4 in which $R^1$ equals H.

8. A compound of claim 2 in which $R^2$ equals the radical of the formula

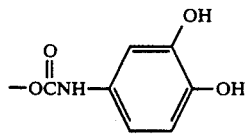

9. The compound of claim 8 in which $R^1$ equals methyl.

10. A compound of claim 3, in which $R^2$ equals the radical of the formula

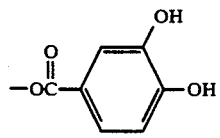

11. The compound of claim 10 in which $R^1$ equals methyl.

12. A pharmaceutical composition comprising an antibacterial effective amount of the compound of claim 5 and a pharmaceutically acceptable carrier or diluent.

13. A pharmaceutical composition comprising an antibacterial effective amount of the compound of claim 6 and a pharmaceutically acceptable carrier or diluent.

14. A pharmaceutical composition comprising an antibacterial effective amount of the compound of claim 7 and a pharmaceutically acceptable carrier or diluent.

15. A pharmaceutical composition comprising an antibacterial effective amount of the compound of claim 9 and a pharmaceutically acceptable carrier or diluent.

16. A pharmaceutical composition comprising an antibacterial effective amount of the compound of claim 11 and a pharmaceutically acceptable carrier or diluent.

17. A method for treating bacterial infection in a mammal, which comprises administering to said mammal an antibacterial effective amount of the compound of claim 5.

18. A method for treating a bacterial infection in a mammal, which comprises administering to said mammal an antibacterial effective amount of the compound of claim 6.

19. A method for treating bacterial infection in a mammal, which comprises administering to said mammal an antibacterial effective amount of the compound of claim 7.

20. A method for treating bacterial infection in a mammal, which comprises administering to said mammal an antibacterial effective amount of the compound of claim 9.

21. A method for treating bacterial infection in a mammal, which comprises administering to said mammal an antibacterial effective amount of the compound of claim 11.

* * * * *